United States Patent [19]
Brereton et al.

[11] Patent Number: 5,963,878
[45] Date of Patent: Oct. 5, 1999

[54] NITRATION PROCESS

[75] Inventors: Clive M. H. Brereton, Richmond; Alfred A. Guenkel, Vancouver, both of Canada

[73] Assignee: Noram Engineering & Constructors Ltd., Vancouver, Canada

[21] Appl. No.: 09/126,087

[22] Filed: Jul. 30, 1998

[51] Int. Cl.[6] ................................................. C07C 205/00
[52] U.S. Cl. ........................... 568/927; 568/932; 568/939
[58] Field of Search ..................................... 568/939, 927, 568/932

[56] References Cited

U.S. PATENT DOCUMENTS 4,310,500  1/1982  Langecker et al. ..................... 423/345
5,756,867  5/1998  Hermann et al. ....................... 568/934

*Primary Examiner*—Gary Geist
*Assistant Examiner*—J. Parsa
*Attorney, Agent, or Firm*—Breiner & Breiner

[57] ABSTRACT

A continuous process to nitrate a nitratable aromatic compound utilizing nitric acid and sulfuric acid feed stocks is described. The process includes the collecting of $NO_x$ o gases with water under pressure to and treating the $NO_x$ gases with water under pressure to produce weak nitric acid which is recycled to the nitric acid feed stock. The process is efficient, permitting the venting of $NO_x$ free gases to the atmosphere.

8 Claims, 2 Drawing Sheets

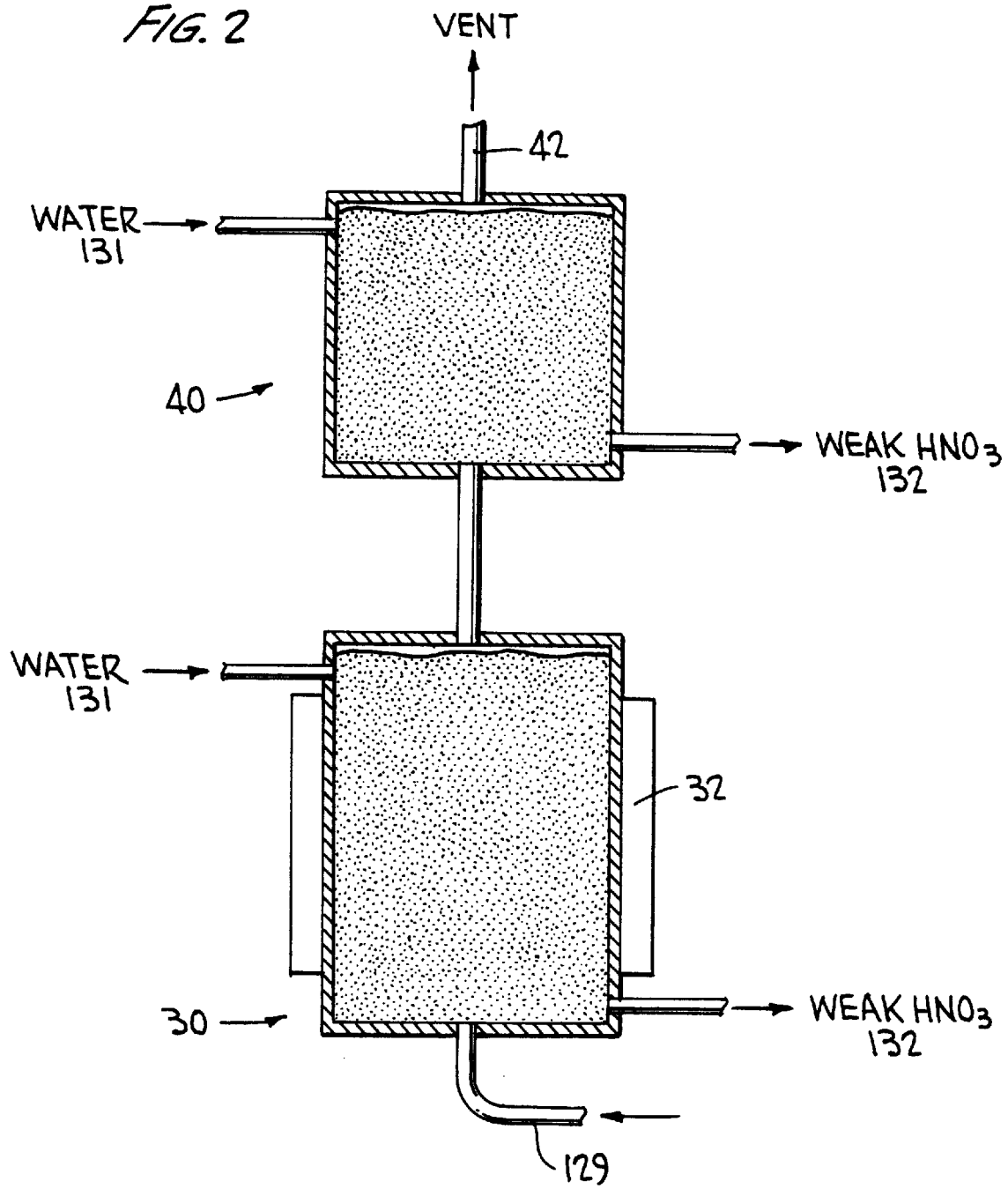

NITRATION PROCESS

FIELD OF INVENTION

This invention relates to an improved continuous process for the nitration of nitratable organic compounds and particularly for the preparation of mononitrobenzene (MNB) from benzene utilizing nitric acid and sulfuric acid feed stocks. According to the improved nitration process, nitrous oxide ($NO_x$) gases produced in the nitration process are collected in water under pressure to produce weak nitric acid which is recycled to the nitric acid feed stock.

BACKGROUND OF INVENTION

Nitrated aromatic hydrocarbons and nitrated halogenated aromatic hydrocarbons and particularly mononitrobenzene are important chemical intermediates. Guenkel et al, U.S. Pat. No. 5,313,009 (the '009 patent), assigned to the assignee of the present invention, describes a continuous process to nitrate a nitratable aromatic compound, typically an aromatic hydrocarbon or a halogenated aromatic hydrocarbon, and particularly benzene, in which the formation of oxidation by-products is substantially reduced compared with the prior art and wherein the reaction rate is substantially increased. The disclosure of this patent, in its entirety, is incorporated herein by reference. According to the process of the '009 patent, $NO_x$ gases are still formed which preferably are not released into the atmosphere for environmental reasons. The prior art has suggested treating these $NO_x$ gases with a caustic solution to form sodium nitrite or sodium nitrate salts, which are disposed of as the salt. Small quantities of $CO_2$ are also formed in the nitration process. $CO_2$ will react with sodium hydroxide to form sodium carbonate; this increases the consumption of sodium hydroxide. Further, the use of sodium hydroxide and formation of salts which must be subsequently disposed of is not completely acceptable on an industrial basis. The discharge of nitrates and especially nitrites of sodium is facing increasingly strict regulation.

The present invention describes a system for removal of $NO_x$ gases which can be utilized in conjunction with the nitration process disclosed in the aforesaid '009 patent, as well as other nitration processes where $NO_x$ gases are formed to efficiently and effectively convert the $NO_x$ gases into weak nitric acid, preferably recycled to the nitric acid feed stock.

SUMMARY OF INVENTION

The present invention provides a continuous nitration process of an aromatic compound such as benzene utilizing nitric acid and sulfuric acid feed stocks wherein $NO_x$ gases produced in the process are contacted with water under pressure and converted to weak nitric acid which is recycled to the nitric acid feed stock. According to the improved process of the invention, $NO_x$ gases are collected from strategic areas of the nitrating system, contacted with air and water, for example, in a packed bed unit at elevated temperature and pressure whereby the $NO_x$ gases are absorbed by the water to form weak nitric acid. The weak nitric acid is recovered from the packed bed unit and recycled to the nitric acid feed stock. $CO_2$ is not absorbed in a $NO_x$ scrubber if the scrubber is operated in an acidic mode. Clean $NO_x$ free vent gas is vented from the packed bed unit. The system is not only effective and efficient, but additionally is cost saving in that the $NO_x$ gases being recovered as nitric acid are reused in the nitration process.

Having described the invention in general terms, the presently preferred embodiment will be described in reference to the drawing.

BRIEF DESCRIPTION OF THE DRAWINGS

In the drawings,

FIG. 2 illustrates two separate but interconnected packed bed sections utilized in contacting the $NO_x$ gases with water to form and concentrate nitric acid for recycling.

DETAILED DESCRIPTION OF PREFERRED EMBODIMENT

Figure 1:
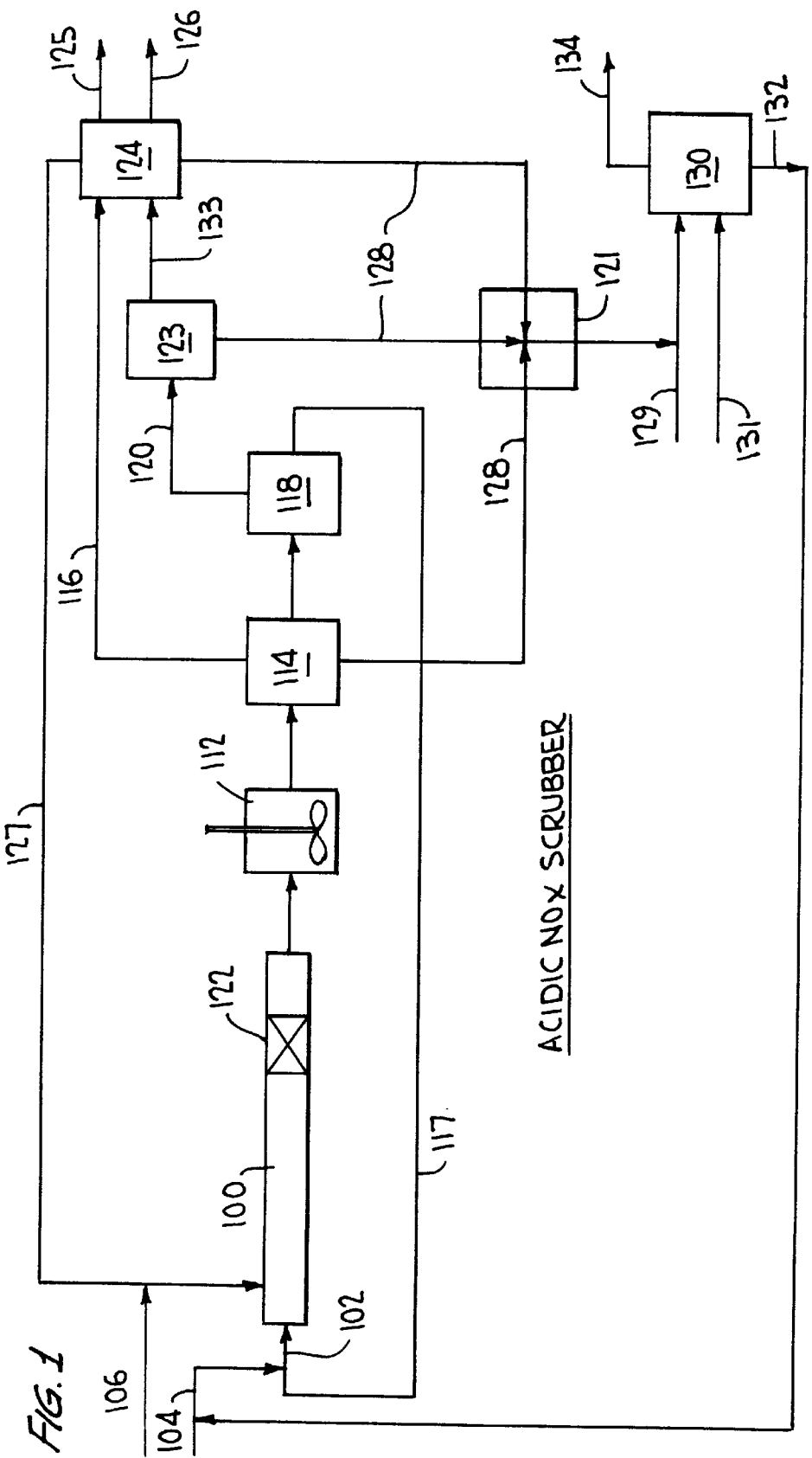
FIG. 1 diagrammatically illustrates a continuous nitrating process carried out in the adiabatic mode, as described in the '009 patent, utilizing the $NO_x$ recovery system of the present invention.

Referring to FIG. 1, a nitration process operating under adiabatic conditions as disclosed in the '009 patent is illustrated. A pipe nitrator 100 receives concentrated sulfuric acid from conduit 102, nitric acid from conduit 104 and hydrocarbon, i.e., benzene, to be nitrated from conduit 106. The acid streams are blended in a ratio such that the resulting mixed acid contains nitric acid mostly in the form of reactive species, i.e., the nitronium ion as described in the '009 patent. The two acid streams from conduits 102 and 104 may be mixed in line before entering the pipe nitrator 100 or they may be introduced separately into the pipe nitrator 100. The pipe nitrator 100 discharges to a stirred tank type nitrator 112. In cases where the reaction rate is very fast, which is specific to the hydrocarbon species to be nitrated and specific to the operating conditions, the reaction may go essentially to completion inside the pipe nitrator 100 so that the stirred tank type of nitrator 112 is not required. In cases where the nitration rate is slow, the pipe nitrator 100 serves mainly as a hydrocarbon dispersion device. Fresh nitrating acid enters the stirred tank nitrator 112 and intimately mixes with fresh hydrocarbon. The process fluids pass to a separator 114 and the nitro product compound is discharged from separator 114 through conduit 116 and fed to a product wash and effluent treatment system 124. Pure nitro organic product, i.e., mononitrobenzene when benzene is treated, is recovered at conduit 125, aqueous effluent is discharged through conduit 126 and some organic recycle is fed by line 127 to hydrocarbon feed 106.

Spent sulfuric acid recovered from separator 114 is delivered to a sulfuric acid concentrator 118. In the sulfuric acid concentrator 118 water is removed via conduit 120 which is fed to a vacuum system 123 while reconcentrated sulfuric acid is recycled to the pipe nitrator 100 through conduit 117.

$NO_x$ gases are drawn off in vacuum system 123 and collected through line 128 at head unit 121. Condensate from vacuum system 123 is fed to product wash and effluent treatment system 124 where additional No, gases are drawn off and fed to head unit 121 through a second line 128. Finally, additional $NO_x$ gases are vented from separator 114 and collected at head unit 121 through a third line 128. All of the $NO_x$ gaseous process vent streams 128, after being combined at head unit 121, are fed to conduit 129 for mixing with air with this mixed stream being fed to a packed bed unit 130 for contact with water 131 to form dilute or weak nitric acid. The weak nitric acid is recycled through line 132 to nitric acid feed stock line 104. Clean $NO_x$ free vent gas is vented from the packed bed through line 134.

As shown in FIG. 2, the $NO_x$ abatement/acid production unit 130 is shown as two separate packed bed sections 30 and 40. The lower packed bed section 30 receives the $NO_x$ gases mixed with air through line 129 and water 131. The $NO_x$ gases, water and air at a pressure of 2 to 5 atmospheres are circulated through packed bed 30 and recovered as weak nitric acid at 132 which is recycled and used as nitric acid stock. This unit will recover approximately 98% of the $NO_x$ gases as weak nitric acid in unit 30. Increased pressure favors increased recovery. A heat exchanger generally at 32 on unit 30 maintains the temperature in unit 30 as low as possible favoring acid production. The second or upper section 40 is used for clean up of the tail gases from first section 30. The second section is a shorter section and is irrigated either with circulating water or caustic. Preferably, caustic is not used in that it will be consumed by $CO_2$. This section receives $NO_x$ tail gases from section 30 at conduit 32 and removes residual $NO_x$ gases to give a colorless stack gas discharged at 42. Depending upon the discharge requirements, the second bed may be either eliminated or, if it is operated with water, may feed to the first bed. The liquid effluent is combined with other weak processing effluents for recycling through line 132. The packed bed sections are operated at pressures which vary from 2 to 5 atmospheres as above stated. Typically, the weak nitric acid formed for recycling will vary in strength from 2 to 10 weight percent, depending upon the requirements of the process. Thus, in the aforesaid system, the $NO_x$ collection will be carried out at the temperature and pressure of the nitrating process. However, the pressure in the unit for forming dilute nitric acid will preferably be at an elevated pressure selected to accommodate most efficient formation of nitric acid under the other conditions of the nitrating process.

As will be apparent to one skilled in the art, although the present invention is described with the specific process disclosed in the '009 patent, it can be used in any of the known prior art nitrating systems where nitration is accomplished with nitric acid and sulfuric acid feed stocks and $NO_x$ gases are formed. Other nitrating systems are described in the '009 patent under the heading "Description of the Prior Art." As will also be apparent to one skilled in the art, the $NO_x$ gases, depending upon the particular system employed, may be recovered at various points in the nitration system. While the $NO_x$ gases are converted to nitric acid in a packed bed system, as above described, other systems can be utilized, it only being essential that the $NO_x$ gases are brought into contact with water, preferably under pressure, so as to form weak nitric acid. These modifications, being known to known to one skilled in the art, are to be covered by the appended claims.

It is claimed:

1. A continuous process to nitrate a nitratable aromatic compound comprising:
   a) introducing a nitratable aromatic compound, nitric acid and sulfuric acid into a nitrator;
   b) reacting said nitratable aromatic compound, nitric acid and sulfuric acid under controlled conditions to produce a nitrated aromatic compound and $NO_x$ gases;
   c) separating said $NO_x$ gases from said nitrated aromatic compound;
   d) contacting said $NO_x$ gases with pure water or essentially pure water under elevated pressure to form weak nitric acid, and
   e) recycling said nitric acid for reuse in the process.

2. The process of claim 1 wherein said nitratable aromatic compound is benzene and the nitrated aromatic compound is mononitrobenzene.

3. The process of claim 2 wherein said $NO_x$ gases are contacted with water under pressure in a packed bed system.

4. The process of claim 3 wherein said packed bed system comprises two separate but connected packed beds.

5. A nitration system comprising a nitrator for nitrating a nitratable aromatic compound, including feed means for feeding each of a nitratable aromatic compound, nitric acid feed stock and sulfuric acid feed stock into said nitrator; separator means for separating a nitrated aromatic compound from spent sulfuric acid; means for separating $NO_x$ gases from said nitrated aromatic compound, and means for contacting said $NO_x$ gases with pure water or essentially pure water under elevated pressure to form weak nitric acid.

6. The nitration system of claim 5 wherein said nitratable aromatic compound is benzene.

7. The nitration system of claim 6 wherein said nitrator further includes a product wash and effluent system and means for separating and collecting $NO_x$ gases therefrom.

8. The nitration system of claim 7 wherein said nitrator further includes a vacuum system for receiving nitrated aromatic compound and water and means for separating and collecting $NO_x$ gases therefrom.

* * * * *